United States Patent
Sjöholm

(10) Patent No.: US 6,394,992 B1
(45) Date of Patent: *May 28, 2002

(54) ASEPTIC CONNECTION DEVICE

(75) Inventor: Johan Sjöholm, Lund (SE)

(73) Assignee: Arom Pak International AB, Lund (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/480,646

(22) Filed: Jan. 11, 2000

Related U.S. Application Data

(63) Continuation of application No. PCT/SE98/01373, filed on Jul. 13, 1998.

(30) Foreign Application Priority Data

Jul. 14, 1997 (SE) .............................................. 9702690

(51) Int. Cl.[7] .............................................. A61B 19/00
(52) U.S. Cl. ...................... 604/411; 604/198; 604/905; 604/199; 141/329; 141/313; 285/3; 285/4; 285/93
(58) Field of Search ................................ 604/533–535, 604/411, 412, 414, 246, 171, 256, 192, 905, 198, 201, 236, 199, 244, 249, 164.08, 167.02, 167.03, 167.04; 141/329, 313; 285/3, 4, 93

(56) References Cited

U.S. PATENT DOCUMENTS

| 3,902,489 | A | * | 9/1975 | Carter .................... 128/214 R |
|---|---|---|---|---|
| 3,986,508 | A | | 10/1976 | Barrington |
| 4,201,208 | A | * | 5/1980 | Cambio, Jr. |
| 4,457,749 | A | * | 7/1984 | Bellotti et al. ................ 604/29 |
| 4,458,733 | A | * | 7/1984 | Lyons ........................... 141/1 |
| 4,564,054 | A | * | 1/1986 | Gustavsson ................. 141/329 |
| 5,067,950 | A | * | 11/1991 | Broadnax, Jr. .............. 604/317 |
| 5,086,813 | A | * | 2/1992 | Galloway ....................... 141/1 |
| 5,117,875 | A | * | 6/1992 | Marrucchi ..................... 141/1 |
| 5,122,123 | A | * | 6/1992 | Vaillancourt ................ 604/192 |
| 5,176,673 | A | | 1/1993 | Marrucchi |
| 5,330,448 | A | | 7/1994 | Chu |
| 5,380,306 | A | * | 1/1995 | Brinon ....................... 604/244 |
| 5,492,147 | A | * | 2/1996 | Challender et al. .... 137/614.05 |
| 5,501,676 | A | | 3/1996 | Niedospial et al. |
| 5,509,912 | A | * | 4/1996 | Vaillancourt et al. ........ 604/283 |
| 6,063,068 | A | * | 5/2000 | Fowles et al. .............. 604/414 |
| 6,113,068 | A | * | 9/2000 | Ryan ....................... 251/149.4 |

FOREIGN PATENT DOCUMENTS

| EP | 0497229 A1 | | 8/1992 |
|---|---|---|---|
| EP | 0 2560640 | * | 2/1998 |

* cited by examiner

Primary Examiner—Brian L. Casler
Assistant Examiner—Cris Rodriguez
(74) Attorney, Agent, or Firm—Birch, Stewart, Kolasch & Birch, LLP

(57) ABSTRACT

A connection device includes a first connecting device and a second connecting device, which are interconnectible for the purpose of transferring an aseptic fluid. The first connecting device includes an injection needle and a protecting sleeve which has an orifice that can be punctured and which at least partially surrounds the needle and is displaceable relative thereto. The second connecting device includes a rubber-like part, which is penetratable by the needle and resealable when the needle is withdrawn.

8 Claims, 2 Drawing Sheets

ASEPTIC CONNECTION DEVICE

This application is a Continuation of PCT International Application No. PCT/SE98/01373 filed on Jul. 13, 1998, which designated the United States and on which priority is claimed under 35 U.S.C. §120, the entire contents of which are hereby incorporated by reference.

BACKGROUND OF THE INVENTION

1. Field of the Invention

The present invention relates to a connection device comprising a first connecting means and a second connecting means, which are interconnectible for the purpose of transferring an aseptic fluid. The invention also concerns a connecting means for such a device, and an aseptic connection device between a) an aseptic fluid storage comprising connecting means and b) means for aseptic supply of said fluid to a device.

2. Description of Background Art

It happens, that small amounts of a fluid which have been prepared in a certain manner, for instance, sterilized, are to be supplied under sterile conditions to a reaction vessel or a process conduit to be caused to contact therein other fluids or gases.

The handling of such preferably aseptic fluids can be effected if the fluid is sterilized in a vessel, the inner sterility of which is controlled. By means of the suggested device, sterilization occurs in a specific place, the fluid being enclosed in bags or plastic containers to be subsequently transported to the place where the fluid is to be used.

SUMMARY OF THE INVENTION

The invention thus concerns a connection device, by means of which it is possible to conveniently interconnect a storage of a fluid, which has been prepared in advance, with the space to which it is to be transported, in fact without affecting the sterility of the fluid.

The invention will now be described in terms of transferring an aseptic fluid to a reaction area, but the invention can be used in several other ways. For instance, it is possible to join a number of fluids with each other in a manner here described, and it is also possible to use, not only aseptic fluids, but also such fluids as spread odour, poison, bacteria and other non-desirable substances. Of course it is possible to use the inventive connection device between different types of devices and for flows in optional directions.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by means of three Figures, of which FIG. 1 shows schematically how a treatment chamber is connected to a first connecting means and a storage is connected to a second connecting means.

DESCRIPTION OF PREFERRED EMBODIMENTS

Figure 1:
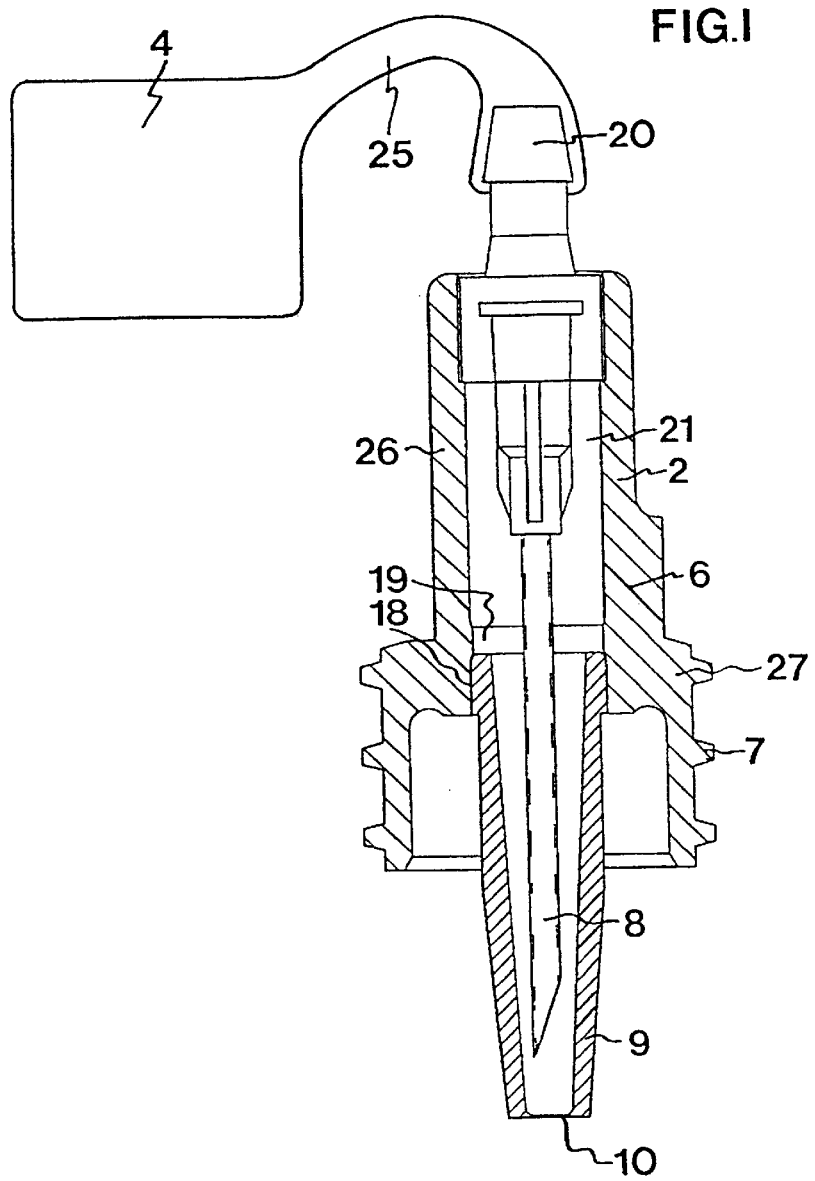
FIG. 1 illustrates the connection device with two connecting parts which are spaced from each other. Moreover.

The description below follows the drawing which in the present case has been adjusted precisely to the fluids that are to be used.

In the case here described, the use intends to add, for instance, flavorings to a fluid, but the invention can just as well be used to affect another fluid for medicinal purposes.

FIG. 1 shows the device before the interconnecting operation. As is evident from the Figure, the connecting means 2 (male member) is connected to a treatment chamber 4 by means of a tube 25. The treatment chamber may be, for instance, a mixing chamber for adding a first fluid to a second fluid. In the cases where the fluid need be pumped out to yield a uniform flow, it is suitable to connect a pump (not shown) between the treatment chamber 4 and the first connecting means 2. Here only the connecting function will be described.

The first connecting means 2 comprises in the present case a body in the form of a molded or turned plastic body 6, which has an essentially circular-cylindrical part 26 having an inner surface 21. Said circular-cylindrical part 26 is integrated with a lower connecting part 27 with external threads 7. In the means 2, a protecting sleeve 9 is also arranged, which consists of a plastic sleeve intended to surround and protect an injection needle 8 which is inserted into the means 2 and which adjacent to a tube nozzle 20 is attached to the upper portion of the means 2. In the embodiment shown, the needle 8 is fixed to a plug supporting the tube nozzle. The protecting sleeve 9 ensures that sterile surroundings are maintained around the needle 8. The protecting sleeve 9 is, along a sliding portion 18, fixed to the circular-cylindrical part 26 of the first connecting means 2 and is first prevented from sliding along the inner surface 21 by a narrow stop portion 19 which constitutes a narrowed part of the inner surface 21. The outer part of the protecting sleeve 9 is provided with a thin front protective portion 10 at its opening and has a slightly conical front part.

The second connecting means (female member) 3, which is also shown in FIG. 1, is also made of a plastic material, preferably of the same type as the material of the means 2. The second connecting means 3 is fixed in a storage means 5 of the type that is to be used when effecting the operation, and may vary in many different ways. The second connecting means 3 according to FIG. 1 essentially consists of a holding part 22, an interconnecting part 12, a receiving part 17 for the above-mentioned protecting sleeve 9, and a portion having internal threads 13. The second connecting means 3 also comprises a rubber-like plug 15 which is arranged in an insert and is adapted to seal the lower part of the second connecting means 3. The plug 15, which is exchangeable, is adapted to be fixed in a recess in the connecting means 3. The holding part 22 is primarily intended to connect the connecting means 3 with a joining means, such as the storage means 5, and can, in other embodiments, be formed in some other suitable manner.

The threaded portions 7, 13 of the two connecting means constitute first and second coupling means to keep the means 2, 3 releasably coupled together. The coupling means can also be designed in other alternative ways, for instance with a bayonet joint.

Figure 3:
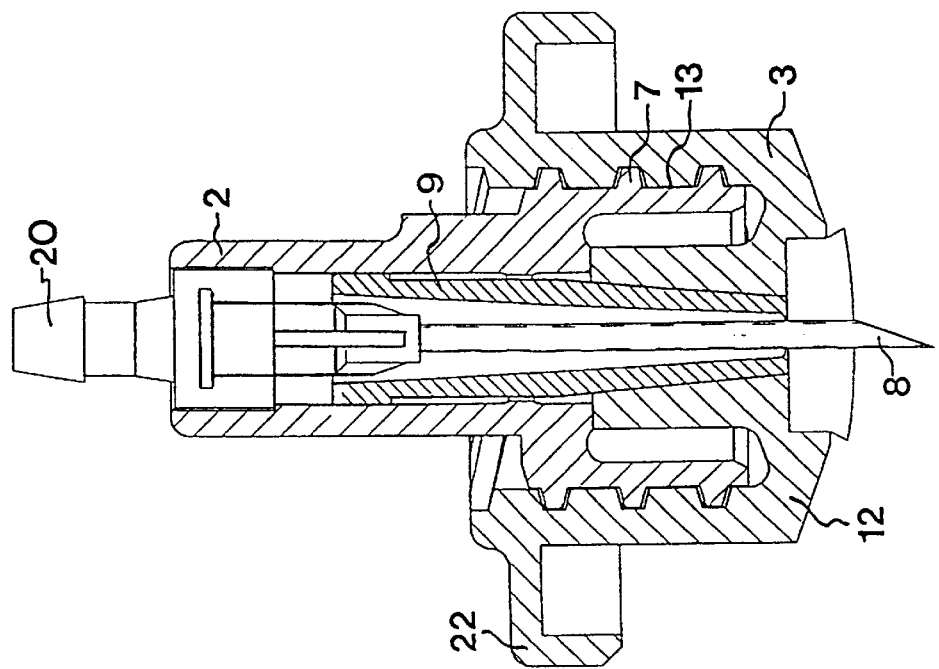
FIG. 3 shows the connection device in the interconnected state.
Figure 2:
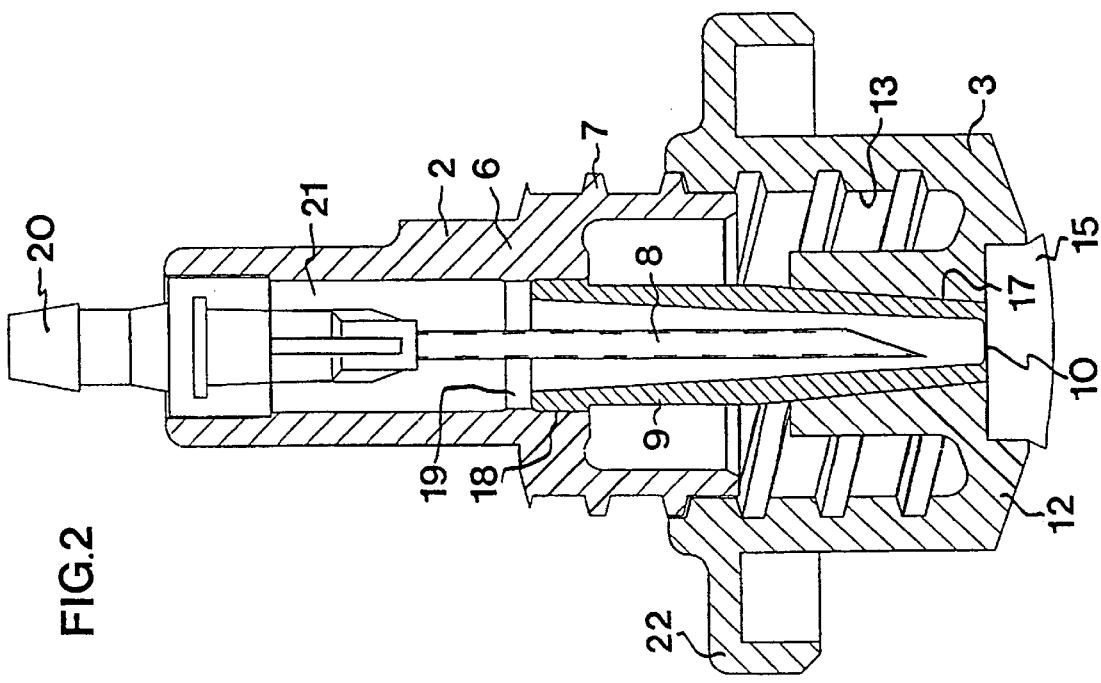
FIG. 2 shows the two connecting means of the connection device in the state intended for interconnection.

In FIGS. 2 and 3, the means 4,5 connected with the two connecting means of the connection device have been excluded. These Figures merely show how the two parts for aseptic transfer of fluid function.

FIG. 2 shows the connection device in the state where the threads 7 and 13 match each other, but where the protecting sleeve 9 has reached its bottom position by being clamped in the conical hole 17 with its front end wall 10 edge-to-edge with the rubber-like part 15.

In FIG. 2, the first connecting means 2 (male member) is screwed into the second connecting means (female member) a few turns, and the protecting sleeve 9 has reached its bottom position in the receiving part 17. If the threads are turned further, the upper connecting means 2 is pressed further downwards, whereas the protecting sleeve 9, which cannot advance further downwards, is pressed upwards past the stop portion 19 while the injection needle 8 cuts through the opening portion 10 of the protecting sleeve 9 and is pressed further through the rubber plug 15 which encloses the injection needle 8 in a tight fit.

FIG. 3 shows the end position of the device, in which the injection needle 8 is pressed through both the front part of the protecting sleeve 9 and through said rubber part 15 so as to then penetrate into the interior of the container 5 for receiving or discharging fluid 1. The injection needle 8 now has a free space to transport aseptic fluid 1 from the storage 5 to the treatment chamber 4.

If the operation is to be terminated while there is still some aseptic material left in the storage container 5, the first connecting means 2 is unscrewed from the second connecting means 3 which retains its aseptic atmosphere by the rubber-like plug 15 aseptically sealing its duct path for the injection needle 8 when this is being withdrawn. When a further fluid transfer from the storage 4 is to be initiated, it is possible to use a new first connecting means 2, which thus can be used as a disposable product. For maintaining sterility, the second connecting means 2 is sealed on its side facing away from the protecting sleeve 9, either immediately adjacent to the tube nozzle or, which is preferred, at the other end of a connected conduit 25.

The connection device according to the invention has been found extremely advantageous when transferring an aseptic fluid to or from a storage which has flexible walls and is of the collapsing type. The rubber-like part of the second connecting means is advantageously connected directly to one of the flexible walls of the storage. The connection device functions excellently when transferring fluid in an optional direction and between two means of an optional kind. For instance, the invention is applicable in fluid transfer to a treatment chamber from a conduit connected to the first connecting means to a chamber connected to the second connecting means. The first connecting means further has great advantages also without cooperation with a second connecting means, for example when transferring fluid through a penetratable membrane.

By using the inventive method, it is possible to economise on sterile fluid in a satisfactory manner, and it is also possible to distribute the production of sterile fluid. Thus the sterile fluid need not at all be prepared by the user, but can be bought when required in bottles or plastic bags.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A connection device for a storage containing an aseptic fluid, comprising:

a transferring device connectable to the storage, said transferring device comprising:
a first means for connecting provided with connecting threads;
an injection needle centrally located and connected in said first means for connecting; and
a protecting sleeve surrounding said injection needle and movable into said first means for connecting in a direction of said injection needle along a fitting against an inside of said first means for connecting, said protecting sleeve being provided with a protective portion which can be punctured; and means for aseptic supply connectable to said transferring device for transferring the fluid under aseptic conditions between the storage and a chamber via said connection device, said means for aseptic supply comprising:
a second means for connecting provided with threads adapted to receive said connecting threads of said first means for connecting, said second means for connecting having an opening corresponding to a tapering front part of said protecting sleeve; and
a plug arranged at a bottom of said second means for connecting, said plug being easily penetratable by said injection needle and, when said needle is being withdrawn during termination of a connection between said first means for connecting and said second means for connecting, said plug again forms an aseptic seal.

2. The connection device as claimed in claim 1, wherein said means for aseptic supply comprises an insert for said plug.

3. The connection device as claimed in claim 1, wherein said first means for connecting is replaceable in case of a repeated process.

4. The connection device as claimed in any one of claims 1–3, wherein said second means for connecting further comprises:
a receiving part having a conical hole for receiving said protecting sleeve, said plug being arranged at a bottom of said receiving part;
said needle has an outer, obliquely cut end; and
said receiving part is arranged for clamping said protecting sleeve when said first means for connecting is connected to said second means for connecting.

5. A connection device for a storage containing an aseptic fluid, comprising:

a transferring device connectable to the storage, said transferring device comprising:
a first device provided with connecting threads; an injection needle centrally located and connected in said first device; and
a protecting sleeve surrounding said injection needle and movable into said first device in a direction of said injection needle along a fitting against an inside of said first device, said protecting sleeve being provided with a protective portion which can be punctured; and an aseptic supply device connectable to said transferring device, said aseptic supply device being capable of transferring the fluid under aseptic conditions between the storage and a chamber via said connection device, said aseptic supply device comprising:

a second device provided with threads adapted to receive said connecting threads of said first device, said second device having an opening corresponding to a tapering front part of said protecting sleeve; and a plug arranged at a bottom of said second device, said plug being easily penetratable by said injection needle and, when said needle is being withdrawn during termination of a connection between said first device and said second device, said plug again forms an aseptic seal.

6. The connection device as claimed in claim 5, wherein said aseptic suply device comprises an insert for said plug.

7. The connection device as claimed in claim 5, wherein said first device is replaceable in case of a repeated process.

8. The connection device as claimed in any one of claims 6–7, wherein said second device further comprises:

a receiving part having a conical hole for receiving said protecting sleeve, said plug being arranged at a bottom of said receiving part;

said needle has an outer, obliquely cut end; and said receiving part is arranged for clamping said protecting sleeve when said first device is connected to said second device.

* * * * *